United States Patent
Warner et al.

(10) Patent No.: US 10,172,563 B2
(45) Date of Patent: Jan. 8, 2019

(54) METHOD AND SYSTEM FOR ANALYZING NOISE IN AN ELECTROPHYSIOLOGY STUDY

(71) Applicant: General Electric Company, Schenectady, NY (US)

(72) Inventors: Adrian F. Warner, Wauwatosa, WI (US); Claudio P. Mejia, Wauwatosa, WI (US); Daniel R. Schneidewend, Wauwatosa, WI (US); Timothy P. Stiemke, Wauwatosa, WI (US); Payam Karbassi, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 603 days.

(21) Appl. No.: 13/934,723

(22) Filed: Jul. 3, 2013

(65) Prior Publication Data

US 2015/0012222 A1    Jan. 8, 2015

(51) Int. Cl.
| | | |
|---|---|---|
| *G01N 33/48* | (2006.01) | |
| *A61B 5/00* | (2006.01) | |
| *A61B 5/04* | (2006.01) | |
| *G06G 7/58* | (2006.01) | |
| *G06F 19/24* | (2011.01) | |
| *G01N 33/66* | (2006.01) | |
| *G06F 19/22* | (2011.01) | |

(52) U.S. Cl.
CPC ........ *A61B 5/7203* (2013.01); *A61B 5/04012* (2013.01); *G01N 33/66* (2013.01); *G06F 19/22* (2013.01); *G06F 19/24* (2013.01)

(58) Field of Classification Search
None
See application file for complete search history.

(56) References Cited

U.S. PATENT DOCUMENTS

| | | |
|---|---|---|
| 3,858,575 A | 1/1975 | Rose |
| 5,010,887 A | 4/1991 | Thornander |
| 2010/0317983 A1 | 12/2010 | Vajdic |
| 2011/0224988 A1 | 9/2011 | Mahajan et al. |

*Primary Examiner* — Eric S Dejong
(74) *Attorney, Agent, or Firm* — Grogan, Tuccillo & Vanderleeden, LLP

(57) ABSTRACT

A method for analyzing noise in an electronic signal monitoring study includes selecting a study signal for analysis, removing a study subject's physiological signal from the study signal, and performing a quantitative analysis on the study signal. A fingerprint of any noise present in the study signal is then created.

11 Claims, 4 Drawing Sheets

METHOD AND SYSTEM FOR ANALYZING NOISE IN AN ELECTROPHYSIOLOGY STUDY

BACKGROUND

Technical Field

Embodiments of the invention relate generally to electronic signal monitoring and more specifically to methods for analyzing noise in an electrophysiology study.

Discussion of Art

Electrocardiography (ECG) studies record the electrical activity and pathways of a heart to identify, measure and diagnose arrhythmias. To accomplish this, ECGs utilize electrodes that are combined into pairs, the output of which are referred to as a lead. ECG leads are used in electrophysiology (EP) studies, which assess electrical activity through the use of catheters placed in the heart through veins or arteries. More specifically, surface ECG leads attached to the patient are used as the reference for the intra cardiac signals from the catheters. That is, they apply a voltage reference to the patient for measurement by other leads.

In the electrophysiology context, ECG and intra cardiac leads may encounter line frequency noise, magnetic noise and/or noise from muscle tremor. Study noise may result from the use of wireless electrical devices, ablation equipment, the attachment of multiple medical devices to a subject, ungrounded electrical extension cords, electrical sockets, high-energy consumption equipment, and the like. In addition, the leads have to measure relatively small electrical signals from the patient, less than 20 uV in some instances. As will be appreciated, given the above considerations, achieving acceptable study recordings may be challenging and eliminating/reducing study noise is an important consideration.

In view of the above, it is desirable to accurately and efficiently identify sources of noise, and quantify the effects of noise, in electronic signal monitoring studies such as EP studies and the like, so that the sources may be removed.

BRIEF DESCRIPTION

In an embodiment, a method for analyzing noise in an electronic signal monitoring study includes selecting a study signal for analysis, removing a study subject's physiological signal from the study signal, and performing a quantitative analysis on the study signal. A fingerprint of any noise present in the study signal is then created.

In an embodiment, a method for analyzing noise in an electrophysiology study includes selecting a study signal for analysis, removing a study subject's cardiac signal from the study signal, performing a power spectral density analysis on the study signal. A fingerprint creating of any noise present in the study signal is then created.

In an embodiment, system for analyzing noise in an electronic signal monitoring study includes a controller and a user interface operatively connected to the controller. The controller contains a set of instructions that it can execute to receive an electronic signal from a study subject, remove the subject's physiological signal from the signal, perform a quantitative analysis on the signal and create a noise fingerprint.

DRAWINGS

The present invention will be better understood from reading the following description of non-limiting embodiments, with reference to the attached drawings, wherein below:

DETAILED DESCRIPTION

Figure 2:
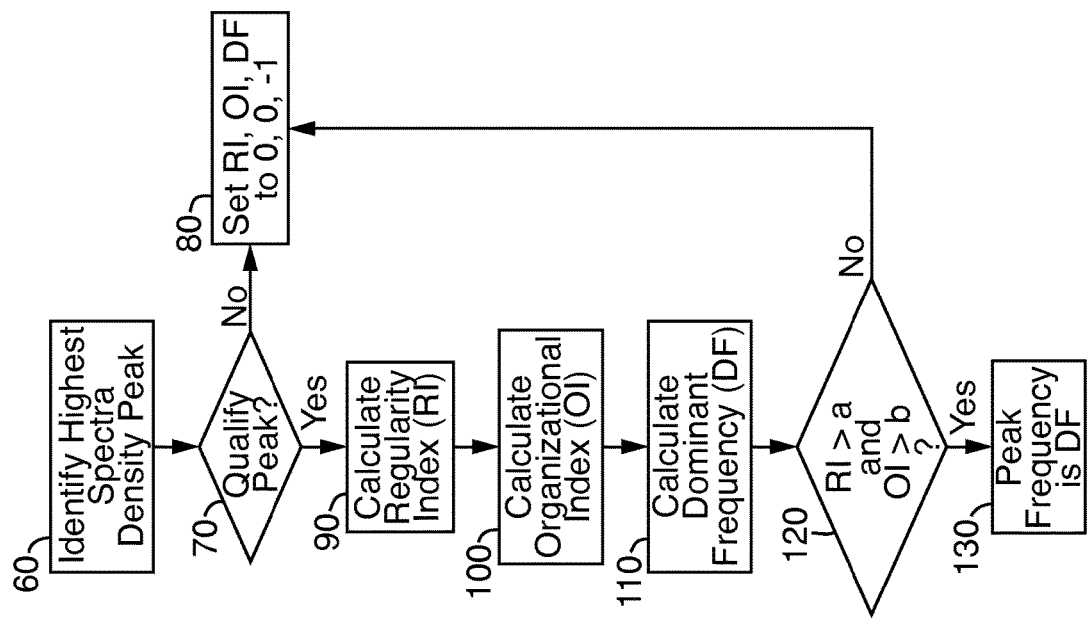
FIG. 2 is a flowchart depicting a method of analyzing power spectral density peaks to create a signal fingerprint, according to an embodiment of the invention.

Reference will be made below in detail to exemplary embodiments of the invention, examples of which are illustrated in the accompanying drawings. Wherever possible, the same reference characters used throughout the drawings refer to the same or like parts. Although embodiments of the present invention are described as intended for use with electrocardiograph systems, it will be appreciated that embodiments may be adapted for use with other electronic signal monitoring systems that encounter noise, wander, and/or other performance affecting phenomena. These may include, but are not limited to, electro encephalogram, electroneurogram, and electromyogram systems.

Moreover, embodiments of the system can be used with various ECG signal acquisition applications such as ECG monitoring in an EP study, stress test ECG, resting ECG, exercise ECG, patient monitoring, defibrillators, etc. involving, sensitive electrical signal recording and processing. Types of noise may include, but are not limited to, noise resulting from muscle tremor, line frequency, and/or magnetic noise, among other sources. Such noise may result from the use of ablation equipment, the attachment of multiple medical devices to a subject, ungrounded electrical extension cords, electrical sockets, high-energy consumption equipment, and the like. Embodiments of the inventive system are intended for use in testing subjects, which, as will be appreciated, may be animals or humans.

Figure 1:
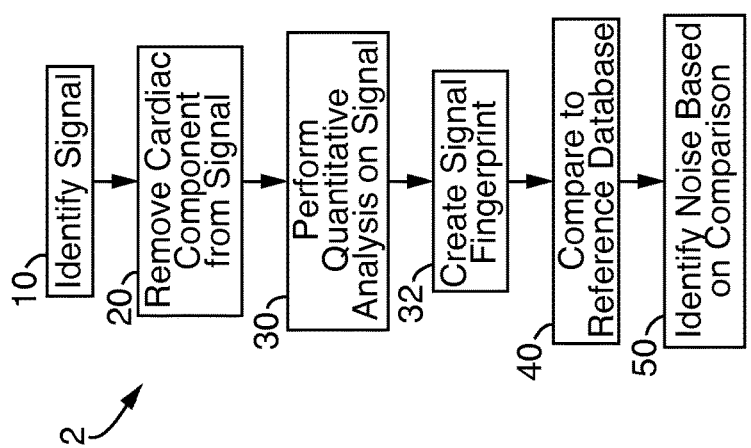
FIG. 1 is a flowchart depicting a method of analyzing noise in accordance with an embodiment of the present invention.

Referring now to FIG. 1, an embodiment of the inventive method is graphically depicted. As shown, the method 2 includes an initial step 10 in which a signal to be analyzed is selected or identified. The signal may be greater than a predetermined duration threshold duration, such as 1 second. The signal may be a surface ECG signal, an intra cardiac signal or a pressure signal. In other embodiments, signals from various other electronic signal monitoring systems, e.g., an electroneurogram or electromyogram, may be identified for analysis.

In embodiments, the signal to be analyzed is identified or selected in real time or near real time, i.e., directly from the signal acquisition system computer during the study. In other embodiments, the signal may be selected from study data that has been prerecorded and stored in a storage device such as a solid-state drive. If the data is prerecorded, embodiments of the invention can be used to provide a retrospective signal noise analysis.

After the signal has been identified, the cardiac component of the signal is removed at step 20. That is, the study subject's own physiological signal is removed so that only noise, if present, remains. In an embodiment, R-wave amplitude from the QRS complex is first detected using a peak detector. A region of interest from between R-waves is then selected. The region of interest being a baseline quiescent period having none of the subject's physiological electrical impulses. Data in the region of interest is then sampled for further analysis.

At step 30, a quantitative analysis is performed on the sampled signal data. In an embodiment, spectral analysis is performed on the data. In particular, a power spectral density analysis calculated through the use of, for example, a Welch method. The power spectra density may then be smoothed using a moving average. In other embodiments, a power spectral density analysis may be accomplished through other Fourier transform based methods, such as a periodogram or multitaper method. In yet other embodiments, instead of a power spectral density analysis, a mean square spectrum, or time-frequency signal representation using a spectrogram function may be used.

Once the quantitative analysis has been performed, a signal fingerprint is created (step 32). As used herein, signal "fingerprint" refers to any electromagnetic signal characteristic or characteristics that allow for the potential identification of a source or class of sources capable of producing that signal. In an embodiment, the signal fingerprint is the power spectra peaks produced as a result of a power spectral density analysis. Other fingerprint types may include, but are not limited to, the degree of noise and the time the noise occurred, noise frequency, standard deviation of noise frequencies, amplitude, etc.

Continuing to refer to FIG. 1, after the signal fingerprint has been obtained, the fingerprint is compared to a database of reference signal fingerprints, e.g., spectra peaks, etc., at step 40. The reference signal fingerprints represent sources of signal noise, or other defining or identifying characteristics of signal noise. For example, there may be a reference signal fingerprint for noise resulting from muscle tremor, line frequency, and/or magnetic noise, among other sources. Accordingly, at step 50, the signal noise is identified based on the signal fingerprint comparison.

The fingerprint comparison may be accomplished by, for example, comparing the signal fingerprint with the reference fingerprint and producing a parameter which quantifies the degree of similarity or dissimilarity between the two. In embodiments, the parameter may be a correlation coefficient.

Referring now to FIG. 2, a method of creating a signal fingerprint according to an embodiment is shown. In particular, a dominant frequency analysis may be utilized to create a spectral peak fingerprint. The first step, step 60, in the dominant frequency analysis is to identify the peak, which involves searching for the highest spectra density peak within a range, such as, for example, between 3 and 30 Hz. The range selected should be broad enough to capture all possible types/sources of noise.

At step 70, the identified peaks are qualified. In an embodiment, qualification involves assessing whether the peak meets certain criteria, e.g., whether the power density value of the half-bandwidth of the peak is less than or equal to the half-height of the peak value. If the peak is not qualified, a dominant frequency (DF) is not found and the DF, OI and RI are set to −1, 0 and 0, respectively (step 80). If qualified, regularity and organization indices are calculated at steps 100 and 110.

Figure 3:
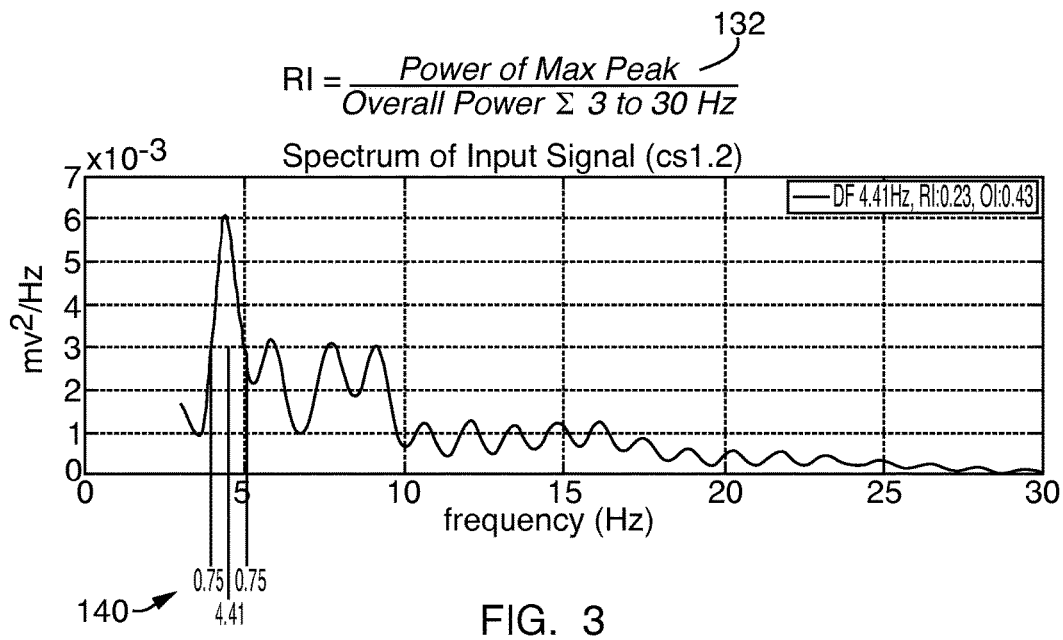
FIG. 3 is a chart depicting computation of a regularity index as part of the method of FIG. 2.
Figure 4:
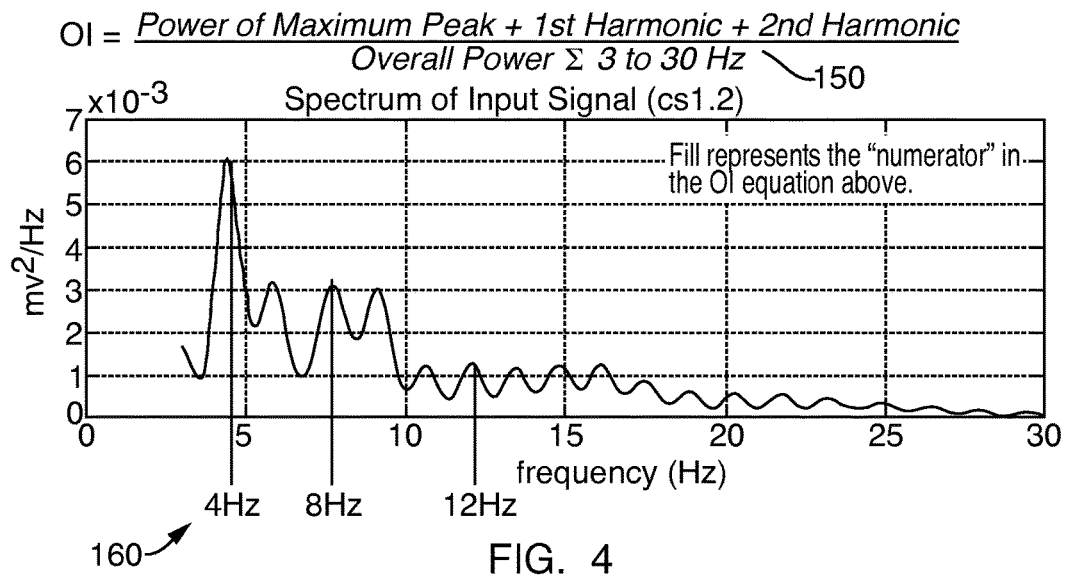
FIG. 4 is a chart depicting computation of an organizational index as part of the method of FIG. 2.

As depicted in FIGS. 3 and 4, the RI is defined as the spectra power within a band, here 0.75 Hz, around the maximum spectra peak 140 divided by the spectra peak between the peak range selected for analysis, e.g., RI=Power of MaxPeak/Overall power Σ3 to 30 Hz (132). The OI is defined as the spectra power within a 0.75 Hz band around the maximum spectra peak 160 and its harmonics divided by the spectra peak range selected for analysis, e.g., OI=(Power of Maximum Peak+$1^{st}$ Harmonic+$2^{nd}$ Harmonic)/Overall power Σ3 to 30 Hz (150).

At step 120, an evaluation is made as to whether the RI and OI are greater than predetermined values a and b, respectively. If they are, then the peak frequency is the dominant frequency. If not, then the DF, OI and RI are again set to −1, 0 and 0. In an embodiment, a is 0.2 and b is 0.25 though other values may be used as where appropriate. The resulting peak dominant frequencies of the signal noise then become the noise fingerprint.

Although dominant frequency peak analysis is described in connection with creating a signal fingerprint, it will be appreciated that many other signal fingerprints may be utilized, and that the invention is not limited to any specific type of signal fingerprint.

Figure 5:
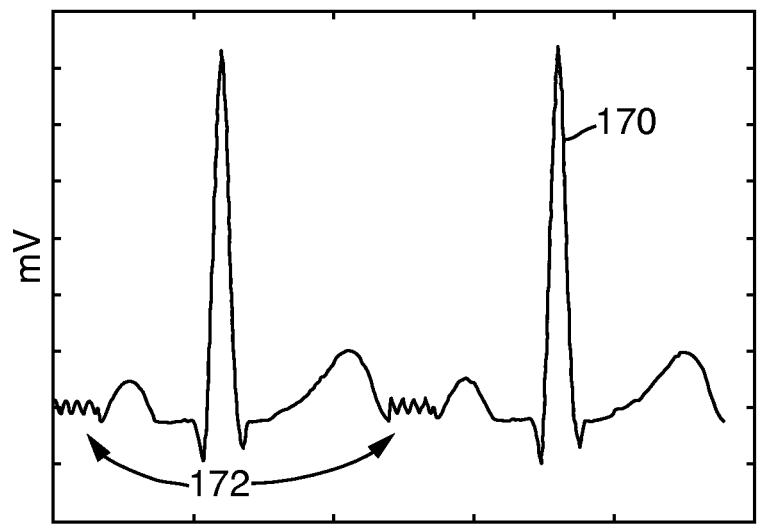
FIG. 5 is a chart depicting an ECG signal that includes a cardiac component as well as noise that may be analyzed according to an embodiment of the present invention.
Figure 6:
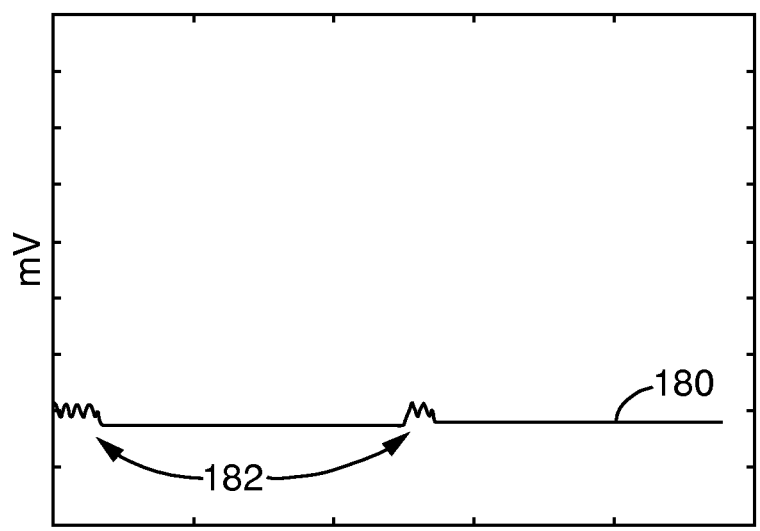
FIG. 6 is a chart depicting the signal of FIG. 5 with the cardiac component removed leaving the noise to be analyzed.
Figure 7:
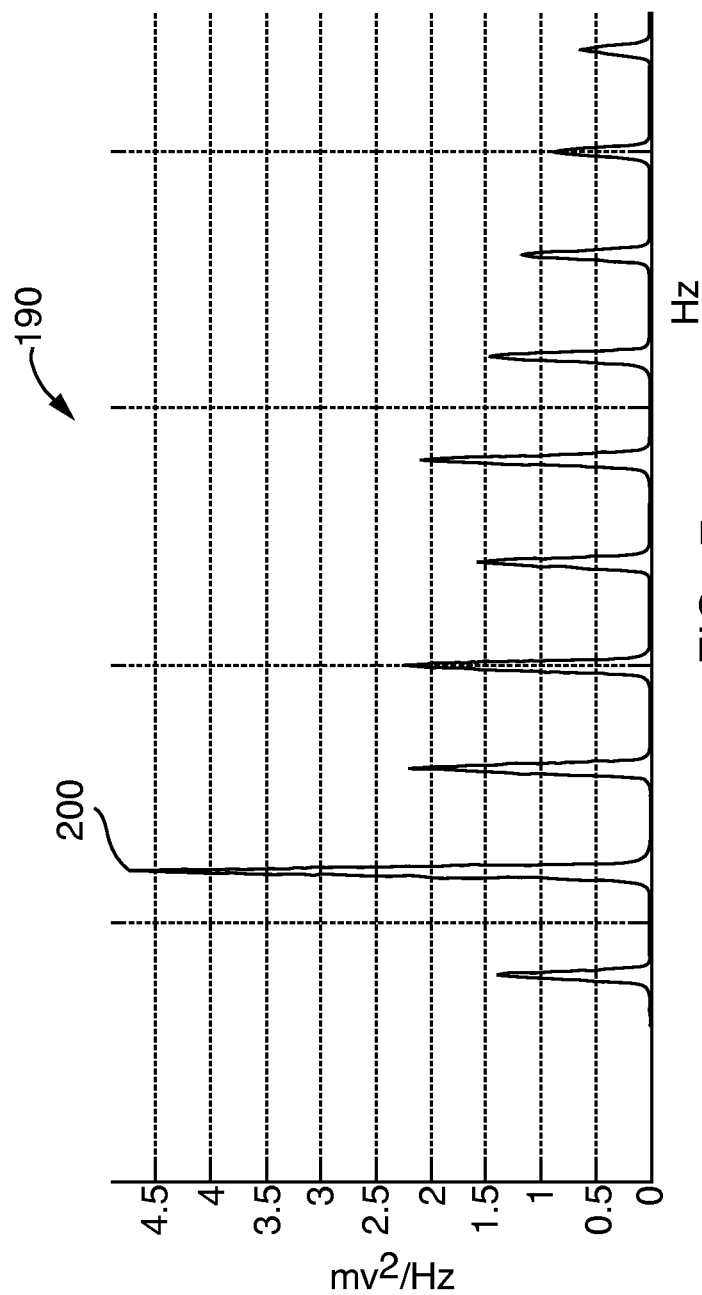
FIG. 7 is a chart depicting a spectral density analysis of the signal of FIG. 6 in accordance with an embodiment of the invention.

Referring now to FIGS. 5-7, the creation of a signal fingerprint according to an embodiment is depicted. In FIG. 5 a subject's signal is depicted. The signal includes the subject's physiological signal, i.e., the cardiac component which includes the QRS complex with two R-waves 170. Once the R-wave amplitude from is detected using, for example, a peak detector, the region, or regions, of interest 172 from between R-waves is then selected. As stated, the region of interest 172 is a baseline quiescent period having none of the subject's physiological electrical impulses.

Once the cardiac component is removed, all that remains in the signal is noise 182 (FIG. 6). A fingerprint of the noise 182 may then be created via a quantitative analysis, using, for example, power spectra density and dominant frequency analyses, or other methods.

FIG. 7 depicts the results of a quantitative analysis, here a power spectral density analysis 190, on the noise 182 from FIG. 6. As shown, multiple peaks 200 are present. Dominant frequency analysis may then be performed on the depicted peaks 200.

It is anticipated that once the source of the noise is identified via a comparison of the fingerprint to the reference fingerprints, that the source will be eliminated. This is in contrast to using filters to eliminate noise from the signal. That said, in certain embodiments, methods of the present invention may be used in connection with or in addition to filters. In certain embodiments, the effects of the noise on the signal may be reduced or mitigated through the use of filters such as Butterworth filters, or through the use of specific noise-reducing circuit topologies.

A system to execute methods of the present invention may, in certain embodiments, be operatively connected to the electronic signal monitoring system, e.g., an electrophysiology system. In such embodiments, the system may include a controller that receives the study subject's signal, and a user interface, such as a computer monitor and keyboard, touch screen, or other human computer interface.

The controller includes a processor that executes a program of instructions to identify the signal, remove the cardiac component, perform a quantitative analysis on the signal, compare the signal to reference signals, and identify the source of noise based on the comparison. The controller may also include, or otherwise be connected to, memory storage, such as a solid-state drive. The memory storage contains the program of instructions to execute embodiments of the invention and may also include the reference fingerprint database.

In certain embodiments, the memory storage may be external to the controller and may be wirelessly connected to the controller. In certain embodiments, the controller may be user programmable to select, for example, the type of quantitative analysis to be performed and/or the data used for the fingerprint. In embodiments, there may be a separate database for the reference fingerprints.

The data from prior studies may be collected and analyzed via a MATLAB® signal processing program. In these embodiments, the data may be stored on a flash drive or the like, or may be transferred wirelessly for further analysis. As will be appreciated, the signal data collected may be analyzed in real time, near real time or retrospectively, depending upon the embodiment.

In an embodiment, a method for analyzing noise in an electronic signal monitoring study includes selecting a study signal for analysis, removing a study subject's cardiac signal from the study signal, performing a quantitative analysis on the study signal and creating a signal fingerprint of any noise present in the study signal. The method further includes comparing the fingerprint to one or more reference noise fingerprints to determine a source of the noise based on the fingerprint comparison. In certain embodiments the noise is then eliminated or reduced. The quantitative analysis may be a spectral analysis and may be a power spectral density analysis. The signal fingerprint includes spectra peaks resulting from the quantitative analysis and a dominant frequency analysis may be conducted on the spectral peaks to create the fingerprint.

A method for analyzing noise in an electrophysiology study includes selecting a study signal for analysis, removing a study subject's cardiac signal from the study signal, performing a power spectral density analysis on the study signal; and creating a signal fingerprint of any noise present in the study signal. The method also includes comparing the fingerprint to one or more reference noise fingerprints and determining a source of the noise based on the fingerprint comparison. The source of noise may then be eliminated or the effects of the noise may be reduced. The signal fingerprint includes spectral peaks resulting from the power spectral density analysis and a dominant frequency analysis has been conducted on the spectral peaks to create the fingerprint.

In an embodiment, a system for analyzing noise in an electronic signal monitoring study includes a controller and a user interface operatively connected to the controller. The controller contains a set of instructions that it can execute to receive a signal from a study subject, remove the subject's physiological signal from the signal, perform a quantitative analysis on the signal and create a noise fingerprint. The system also includes a database operatively connected to the controller and user interface, the database containing one or more reference fingerprint spectra. The controller further contains instructions enabling it to compare the signal fingerprints with the reference fingerprints to identify a source of the noise.

In embodiments, the controller is programmable such that a user may select quantitative analysis from among a plurality of quantitative analyses and/or a type of noise fingerprint from among a plurality of fingerprint types.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. § 122, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for analyzing noise in an electrophysiology signal, the method comprising:
   acquiring the electrophysiology signal via a signal acquisition computer in electronic communication with one or more sensors operative to sense electrical activity produced by a subject, the signal acquisition computer having a controller and a memory storage device, and the electrophysiology signal having a cardiac component and a noise component, the cardiac component generated by the subject and the noise component generated by a source of noise;

removing, via the controller, the cardiac component from the electrophysiology signal;

creating, via the controller, a fingerprint of the noise component after removal of the cardiac component from the electrophysiology signal, the fingerprint comprising of data corresponding to a characteristic of the noise component; and comparing, via the controller, the fingerprint to a database of known fingerprints that each correspond to one or more sources of noise.

2. The method of claim 1 further comprising the step of:

determining the source of the noise component based on the fingerprint comparison.

3. A system for analyzing noise in an electronic signal, the system comprising:

a controller;

an electronic monitoring system that includes a memory storage device and one or more electrodes operative to sense electrical activity produced by a subject, the electronic monitoring system operating in communication with said controller, and operative to acquire a combined signal from the subject via the one or more electrodes, the combined signal having a physiological component and a noise component, the physiological component generated by the subject and the noise component generated by a source of noise;

a user interface operatively connected to the controller;

the controller supporting a set of instructions that it can execute to receive the combined signal from the electronic monitoring system and to remove the physiological component from the combined signal; and wherein a noise fingerprint is generated, via the controller, after removal of the physiological component from the combined signal, the fingerprint comprising of data corresponding to a characteristic of the noise component.

4. The system of claim 3 further comprising:

a database operatively connected to the controller and user interface; and wherein the database contains one or more reference fingerprint spectra.

5. The system of claim 4 wherein the controller further contains instructions enabling it to compare the noise fingerprint with the reference fingerprints to identify the source of the noise component.

6. The system of claim 3 wherein the controller is programmable such that a user may select a type of noise fingerprint from among a plurality of fingerprint types.

7. A method for identifying a source of an unknown extraneous electronic component from a combined signal comprised of a physiological component produced by a subject, and the unknown extraneous component, the method comprising the steps of:

obtaining the combined signal via one or more electrodes operative to sense electrical activity produced by the subject and to electrically communicate with a signal acquisition computer having a controller and a memory storage device;

removing, via the controller, the physiological component from the combined signal;

generating, via the controller, a fingerprint from the combined signal after removal of the physiological component, the fingerprint comprised of data corresponding to a characteristic of the extraneous electronic component;

comparing, via the controller, the fingerprint to a database of known fingerprints of extraneous signals; and identifying, via the controller, the source of the unknown extraneous signal by matching the fingerprint to one of the known fingerprints in the database.

8. The method of claim 7 further comprising:

storing the fingerprint in the database via the controller for future use as one of the known fingerprints.

9. The method of claim 7 wherein the combined signal is an electocardiography signal.

10. The method of claim 7 wherein the characteristic is one or more spectra peaks resulting from quantitative analysis.

11. The method of claim 10 wherein a dominant frequency analysis has been conducted on the spectral peaks to create the fingerprint.

* * * * *